United States Patent [19]
Taylor et al.

[11] Patent Number: 6,075,156
[45] Date of Patent: Jun. 13, 2000

[54] PREPARATION OF CHIRAL CYCLOALKANOLS SUCH AS ENDO-5-NORBORNEN-2-OL

[75] Inventors: Stephen John Clifford Taylor; Raymond McCague; Derek Thomas Edward Jones, all of Cambridge, United Kingdom

[73] Assignee: Chirotech Technology Limited, United Kingdom

[21] Appl. No.: 08/981,940

[22] PCT Filed: Jul. 25, 1996

[86] PCT No.: PCT/GB96/01813

§ 371 Date: Dec. 23, 1997

§ 102(e) Date: Dec. 23, 1997

[87] PCT Pub. No.: WO97/05093

PCT Pub. Date: Feb. 13, 1997

[30] Foreign Application Priority Data

Jul. 26, 1995 [GB] United Kingdom ............... 9515307

[51] Int. Cl.$^7$ ...................................... C07C 67/00
[52] U.S. Cl. ........................................ 554/161; 568/820
[58] Field of Search ............................ 554/161; 568/820

[56] References Cited

FOREIGN PATENT DOCUMENTS 2854429  6/1980  Germany .

Primary Examiner—Deborah D. Carr
Attorney, Agent, or Firm—Saliwanchik, Lloyd & Saliwanchik

[57] ABSTRACT

A cycloalkanol is prepared by cycloaddition between a diene and a vinyl ester, wherein the ester is derived from a carboxylic acid of sufficient molecular weight to enable the reaction to be carried out at atmospheric pressure while above 150° C., and the corresponding reaction between the diene and vinyl acetate generates a pressure above 4 atmospheres.

12 Claims, No Drawings

PREPARATION OF CHIRAL CYCLOALKANOLS SUCH AS ENDO-5-NORBORNEN-2-OL

This application is a 371 of PCT/OD96/01813 filed Jul. 25, 1996.

FIELD OF THE INVENTION

This invention relates to a process for the manufacture of endo-5-norbornen-2-ol or related cycloalkanols as their racemates or as their enantiomers.

BACKGROUND OF THE INVENTION

Racemic endo-5-norbornen-2-ol can be obtained by heating dicyclopentadiene with vinyl acetate. The reaction requires a high temperature (typically >160° C.) at which the dicyclopentadiene is in equilibrium with the monomer cyclopentadiene that then undergoes Diels-Alder cycloaddition with the vinyl acetate. Pre-cracked cyclopentadiene cannot be used, as it dimerises faster than it reacts with the vinyl acetate. A consequence of the use of vinyl acetate is that, at the temperature of the reaction, it generates a significant pressure and specialised reactors are needed to contain this. The use of such specialised equipment adds markedly to the process cost.

The enantiomers of the 5-norbornen-2-ol which are of value as intermediates for pharmaceutical agents can be obtained by biocatalytic resolution, typically by treatment of an ester such as the acetate in a water-containing system with a lipase where one enantiomer is hydrolysed preferentially; see Eichberger et al, Tetrahedron Lett. (1986) 27:2843; and Oberhauser et al, Tetrahedron (1987) 43:3931. Alternatively, they can be obtained by biocatalyst-mediated esterification of the racemic alcohol with an acyl donor such as vinyl acetate in an organic solvent.

An issue following such a biotransformation is separation of the products. When these are the norbornenol and its acetate, the separation is difficult owing to the similarity of their physical properties; their boiling points are too similar for separation by distillation. While chromatographic separation is effective, that is not amenable to large-scale operation.

SUMMARY OF THE INVENTION

This invention is based in part on the realisation that an easier separation of the products from a biocatalytic resolution of endo-5-norbornen-2-ol should result if the ester is derived from a higher molecular weight carboxylic acid than is the acetate. Where the feedstock is derived from the vinyl acetate cycloaddition, then either the ester has to be exchanged for another, or the acetate has to be hydrolysed to the alcohol and that esterified under biocatalysis with a donor such as vinyl butyrate. The norbornenol and esters such as the butyrate thus derived were separable readily by either distillation or partitioning between water and a hydrophobic organic solvent such as heptane. In principle, the appropriate substrates for the hydrolytic mode of biotransformation could be obtained by carrying out the cycloaddition with a higher vinyl ester such as vinyl butyrate, vinyl hexanoate, or vinyl laurate. Such higher vinyl esters are readily available as a result of their use as monomers in the polymer industry.

It has been discovered that these higher vinyl esters were effective in the cycloaddition reaction with cyclopentadiene, surprisingly forming the required product as cleanly as did the vinyl acetate, despite the addition of the extra carbons which might have been thought to reduce reactivity and give more opportunities for unwanted reactions. Moreover, when the vinyl ester was vinyl hexanoate or a higher ester, the cycloaddition reaction could be performed without a pressure vessel, simply by heating a mixture of cyclopentadiene and the vinyl ester at reflux. The product, e.g. 5-norbornen-2-yl hexanoate, was then available directly as a substrate for the biotransformation; the product (R)-endo-norbornenol from that biotransformation, using an enzyme such as *Candida cylindracea* lipase (CCL), was easily separable from the residual ester by distillation.

As a further feature of this invention, it has been discovered that the higher vinyl esters transformed with the CCL biocatalyst at a greater rate than the acetate for a given amount of enzyme. This in turn results in improved process cost through the saving in time or saving in enzyme (less enzyme used for the same time period).

Therefore, according to one aspect of this invention, a process for preparing a cycloalkanol by cycloaddition between a diene and a vinyl ester, wherein the ester is derived from a carboxylic acid of sufficient molecular weight to enable the reaction to be carried out at atmospheric pressure while above 150° C., and the corresponding reaction between the diene and vinyl acetate generates a pressure above 4 atmospheres.

In a further aspect of the invention, a process for preparing endo-5-norbornen-2-ol is by cycloaddition between cyclopentadiene and a vinyl ester, wherein the vinyl ester is as defined above.

DESCRIPTION OF THE INVENTION

The cycloaddition reaction, whether using vinyl acetate or a higher ester such as the hexanoate, may give not only the endo-cycloadduct but also exo isomer, e.g. in about a 4:1 ratio. This mixture may then be used as the feedstock for biotransformation, where the transformed product was of reduced exo-content as well as predominantly the (R)-enantiomer of the endo-isomer.

A further feature of the invention is the discovery that when the untransformed ester from the biotransformation of predominantly (S)-enantiomer was heated so as to recreate the conditions of its formation, there was observed a degree of racemisation of this material. This might be attributed to reversion of the cycloaddition reaction. This racemised product can then be reused as a substrate in the biotransformation. By this means, most of the material from the cycloaddition can be utilised even when there is a market for one enantiomer.

The overall route is as outlined in Scheme 1.

It follows that dienes other than cyclopentadiene may be used, e.g. in cases where, while cracking of dimer is not an issue, the Diels-Alder cycloaddition requires substantially elevated temperature. In such a case, there is still the need to avoid the use of pressure equipment, i.e. by using a higher vinyl ester. Also, for the bioresolution of the resulting cycloalkanol ester there will be the same issue of separation of cycloalkanol product and ester starting material where there is the benefit of having used a higher vinyl ester in making the enantiomeric products more easily separable. Accordingly, the invention in a more generic form is represented by Scheme 2.

Depending on the reactivity of the diene, any may be chosen. The advantages of the invention are seen when the diene is such that its reaction with vinyl acetate generates a pressure above 4 atmospheres (in an autoclave), and thus relatively expensive pressure equipment is required. As indicated above, the ester group (R') generally has at least 4 C atoms, e.g. 5 to 20 C atoms.

The following Examples illustrate the invention.

EXAMPLE 1

Preparation of norbornenyl hexanoate

Vinyl hexanoate (100 ml) and dicyclopentadiene (15 ml) were brought to reflux under nitrogen (160° C.). Over a period of 24–36 h, a further 9 additions (each 15 ml) of dicyclopentadiene were made, and heating under reflux continued. During this time, the temperature of the boiling liquid increased until after the last addition it was about 205° C. Excess starting materials were then allowed to distil off. After cooling of the mixture to 50° C., methanol (200 ml) was added and the precipitate allowed to form and settle, cooling to 20° C. The ester solution was decanted off and the precipitate washed with a further batch of methanol (100 ml). The methanol solutions were combined and evaporated under reduced pressure at 40–50° C. to yield about 114 g crude norbornenyl hexanoate (estimated molar yield 25% based on the vinyl hexanoate). This material was suitable for biotransformation.

EXAMPLE 2

Bioresolution of norbornenyl hexanoate

Crude norbornenyl hexanoate, prepared as described in Example 1 (784 g, 39% potency). was suspended in 0.1M potassium dihydrogen phosphate buffer at pH 7.8 (2 L). To this was added Amano AY lipase (30 g) and the hydrolysis of the ester maintained by the addition of 10M aqueous sodium hydroxide at 30° C. After 2 days, the conversion was 31%, giving alcohol formed at 86% ee of endo isomer with 12% exo component, and leaving residual hexanoate of 39% ee. The biotransformation was worked up by adjustment to pH 7 with 1M HCl.

The mixture was then distilled under vacuum at approx. 60° C., until about one-third of the original volume remained. The aqueous distillates were combined and then extracted with first 1×100 ml heptane and then 2×50 ml heptane, then saturated with salt and extracted with dichloromethane (4×500 ml). The dichloromethane extracts were concentrated under vacuum to give (R)-endo-5-norbornen-2-ol as a white solid (36.4 g). The heptane extracts contained the (S)-ester and most of the exo isomer.

EXAMPLE 3

Racemisation of norbornenyl hezanoate

Approximately 1 ml norbornenyl hexanoate (81% ee endo isomer and containing about 10% exo isomer) was heated in a sealed vial at 220° C. After 10 days, the enantiomeric excess of endo isomer had dropped to 64% while 21% exo isomer was now present.

EXAMPLE 4

Preparation of norbornenyl laurate

Vinyl laurate (100 ml) and dicyclopentadiene (15 ml) were heated under reflux under nitrogen at 180° C. Over a period of 18 h a further 4 additions of dicyclopentadiene (15 ml) were made; heating was continued so as to maintain 18° C. The mixture was then distilled at 30 mm Hg to remove excess dicyclopentadiene and vinyl laurate. There remained 123 g of the crude norbornenyl laurate which was suitable for bioresolution.

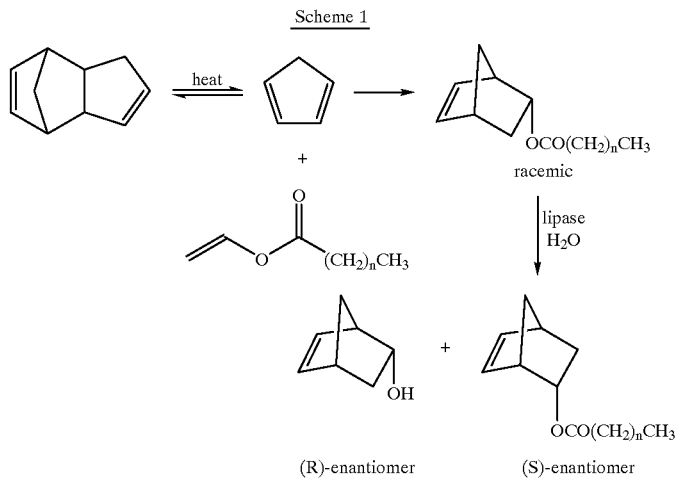

Scheme 1

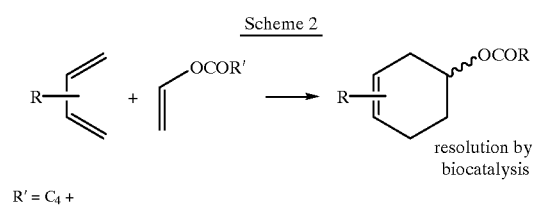

Scheme 2

R' = C₄ +
R = any additional substituents

What is claimed is:

1. A process for preparing an ester of a carboxylic acid and a cycloalkanol, by cycloaddition between a diene and the corresponding vinyl ester;

wherein the carboxylic acid is of sufficient molecular weight to enable the process to be carried out at atmospheric pressure while above 150° C.;

wherein the diene is such that its cycloaddition with vinyl acetate generates a pressure above 4 atmospheres; and wherein the process is conducted at below 4 atmospheres.

2. The process according to claim 1, wherein the diene is cyclopentadiene.

3. A process according to claim 2, for obtaining endo-5-norbornen-2-ol.

4. A process according to claim 1, wherein the vinyl ester has the formula $CH_2=CH-O-CO-R_1$ and $R^1$ has at least 4 C atoms.

5. The process according to claim 4, wherein $R^1$ has 5 to 20 C atoms.

6. The process according to claim 4, wherein the ester is the hexanoate.

7. The process according to claim 4, wherein the ester is the laurate.

8. A process for preparing an enantiomerically-enriched chiral ester cycloalkanol, which comprises the steps of:
   (i) preparing a mixture of enantiomers of an ester of a carboxylic acid and the cycloalkanol, by cycloaddition between a diene and the corresponding vinyl ester, wherein the ester is of sufficient molecular weight to enable the cycloaddition to be carried out at atmospheric pressure while above 150° C., and wherein the diene is such that its cycloaddition with vinyl acetate generates a pressure above 4 atmospheres; wherein the cycloaddition is conducted at below 4 atmospheres; and
   (ii) subjecting the resultant mixture of the enantiomers of the ester to biotransformation with an enzyme containing an appropriate enantiospecificactivity, thereby obtaining either enantiomer of the cycloalkanol.

9. The process according to claim 9, which additionally comprises separation of the cycloalkanol enantiomer, and racemisation of residual cycloalkanol ester of opposite enantiomeric configuration, by heating.

10. The process according to claim 9, wherein the process is conducted at about atmospheric pressure.

11. The process according to claim 1, wherein the process is conducted at about atmospheric pressure.

12. A process for preparing an ester of a carboxylic acid of the formula $R^1$ COOH and 5-norbornen-2-ol, which comprises cycloaddition of cyclopentadiene and a vinyl ester of the formula $CH_2=CH-O-CO-R^1$, wherein $R^1$ has 5 to 20 carbon atoms, and wherein the process is conducted at below 4 atmospheres.

* * * * *

UNITED STATES PATENT AND TRADEMARK OFFICE
CERTIFICATE OF CORRECTION

PATENT NO. : 6,075,156
DATED : June 13, 2000
INVENTOR(S) : Stephen John Clifford Taylor, Derek Thomas Edward Jones, Raymond McCague It is certified that error appears in the above-indentified patent and that said Letters Patent is hereby corrected as shown below:

Column 4, line 63: "ester;" should read --ester,--.

Column 5, line 7: "–CO–R$_1$ and R$^{1}$'" should read -- –CO–R$^{1}$, and R$^{1}$--.

Signed and Sealed this

Third Day of April, 2001

*Attest:*

NICHOLAS P. GODICI

*Attesting Officer*    *Acting Director of the United States Patent and Trademark Office*